(12) United States Patent
De Szalay et al.

(10) Patent No.: US 11,576,880 B2
(45) Date of Patent: Feb. 14, 2023

(54) FEMININE HYGIENE PRODUCTS

(71) Applicant: RB Health (US) LLC, Parsippany, NJ (US)

(72) Inventors: Sarah Frances De Szalay, West Milford, NJ (US); Jessica Wilson, Montvale, NJ (US); Richard Giles, Gothenburg (SE)

(73) Assignee: RB Health (US) LLC, Parsippany, NJ (US)

(*) Notice: Subject to any disclaimer, the term of this patent is extended or adjusted under 35 U.S.C. 154(b) by 0 days.

(21) Appl. No.: 16/343,498

(22) PCT Filed: Oct. 18, 2017

(86) PCT No.: PCT/GB2017/053150
§ 371 (c)(1),
(2) Date: Apr. 19, 2019

(87) PCT Pub. No.: WO2018/078336
PCT Pub. Date: May 3, 2018

(65) Prior Publication Data
US 2019/0262292 A1 Aug. 29, 2019

Related U.S. Application Data

(60) Provisional application No. 62/414,138, filed on Oct. 28, 2016.

(51) Int. Cl.
| | | |
|---|---|---|
| A01N 43/00 | (2006.01) |
| A01N 43/46 | (2006.01) |
| A61K 31/55 | (2006.01) |
| A61K 31/23 | (2006.01) |
| A23K 20/105 | (2016.01) |
| A23K 50/10 | (2016.01) |
| A23K 50/75 | (2016.01) |
| A61K 31/19 | (2006.01) |
| A61P 31/04 | (2006.01) |
| A61K 9/00 | (2006.01) |
| A61K 47/18 | (2017.01) |
| A61K 47/20 | (2006.01) |
| A61K 8/365 | (2006.01) |
| A61Q 19/10 | (2006.01) |
| A61K 31/10 | (2006.01) |
| A61K 8/44 | (2006.01) |
| A61K 8/46 | (2006.01) |
| A61K 31/20 | (2006.01) |

(52) U.S. Cl.
CPC ............. *A61K 31/19* (2013.01); *A61K 8/365* (2013.01); *A61K 8/44* (2013.01); *A61K 8/466* (2013.01); *A61K 9/0034* (2013.01); *A61K 31/10* (2013.01); *A61K 31/20* (2013.01); *A61K 47/18* (2013.01); *A61K 47/20* (2013.01); *A61P 31/04* (2018.01); *A61Q 19/10* (2013.01); *A61K 2800/596* (2013.01); *A61K 2800/70* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,500,460 B1 * | 12/2002 | Bergeron | A61M 35/003 424/486 |
| 2005/0241645 A1 * | 11/2005 | Vernice | A61K 9/0034 128/832 |

FOREIGN PATENT DOCUMENTS

| | | |
|---|---|---|
| CN | 108471742 A | 8/2018 |
| WO | 2007031756 A1 | 3/2007 |
| WO | 2017072482 A1 | 5/2017 |

OTHER PUBLICATIONS

International Search Report and Written Opinion of the International Searching Authority for corresponding application PCT/GB2017/053150 dated Jan. 3, 2018.
Anonymous: "Protective Intimate Soap with Menthol", 12951, Aug. 17, 2016, XP055722435, retrieved from www.gnpd.com.
Anonymous: "Sanitizing Intimate Soap", Mar. 2, 2016, XP055722442, retrieved from www.gnpd.com.
Zhang Zhixiang, "Diagnosis and treatment of digestive diseases", Guangdong Science and Technology Press, Guangzhou, Jul. 2008, ISBN 978-7-5359-4502-0, pp. 501-502.
Zhidong Pang, "Midwives Handbook", 2nd edition, Peoples Medical Publishing House, Oct. 1986, p. 352.
Xian Pan, "New Practical Book of Drugs (Part 1)", 1st edition, China Traditional Chinese Medicine Press, Sep. 1998, p. 886.

* cited by examiner

*Primary Examiner* — Layla Soroush
(74) *Attorney, Agent, or Firm* — Norris McLaughlin PA

(57) ABSTRACT

Disclosed are acidic feminine intimate cleansing compositions having a pH in the range of from 3 to 5, which further necessarily comprises at least: as a primary antimicrobial active constituent, lactic acid, which may optionally be a substituted lactic acid and/or derivative thereof; and which composition further includes an anionic constituent system which boosts the antimicrobial efficacy of the primary lactic acid constituent present; and which compositions feature low irritation, and good antimicrobial efficacy against certain species of bacteria. Treatment processes using the feminine intimate cleansing composition in treatment of the groin area of human females, and vendible products containing the feminine intimate cleansing compositions are also disclosed.

13 Claims, No Drawings

FEMININE HYGIENE PRODUCTS

This is an application filed under 35 USC 371 based on PCT/GB2017/053150 filed 10.Oct.2017, which in turn is based on U.S. Ser. No. 62/414,138 filed 28.Oct.2016. The present application claims the full priority benefit of these prior applications and herein incorporates by reference the full disclosures of these prior applications.

The present invention relates to feminine hygiene compositions which are particularly suited for use as feminine intimate cleansing composition.

Where is there known to the general art of topical cleaning, compositions which are suited as handwash compositions and bodywash compositions are not necessarily particularly desirable for use in intimate cleansing composition for human females. Of particular concern to women are sensitive bodily tissues, particularly in the vaginal region of the female body. Unlike the normal epidermal tissues particularly associated with the hands or upper body, tissues in the vaginal region of the human female body are particularly sensitive to chemicals and are more likely to be prone to undesired irritation which may in some instances even become painful.

The vagina is a dynamic ecosystem that normally contains approximately $10^9$ bacterial colony-forming units per gram of vaginal fluid. The normal vaginal fluid is clear to white, odorless, and of high viscosity. Naturally occurring bacterial flora is incident to the vagina are dominated by Lactobacilli, however, a variety of other organisms, including some potential pathogens, may also be present at lower concentrations. Within the normally healthy human female body, the action of Lactobacilli converts glycogen to lactic acid, whereby the lactic acid produced provides a physiologic lowering of pH. The normal pH level of the vagina of a healthy woman of reproductive age is generally in the range of about 3.8 to about 4.2. This acidic pH level provides a protection by making the vagina less hospitable to certain pathogens, specifically certain yeast and other bacteria, notably including S. aureus which has been associated with "toxic shock syndrome." Additionally it is known that some Lactobacilli also produce hydrogen peroxide which has microbicidal properties that can kill bacteria and viruses. However, the normal balance of microorganisms is disrupted, bacterial vaginosis can occur, leading to vaginal discomfort ranging from itching to a burning sensation along with vaginal discharge. Vaginal discharge is one of the most common conditions for which women seek medical care.

In view of the foregoing, it is apparent that any cleansing composition for female intimate cleansing which would be considered compatible with and effective to treat sensitive bodily tissues of the vaginal region of the female body, as well as the vagina itself, would necessarily need to take into consideration how its use would effect the naturally occurring bacterial flora incident to the vagina, and the normally dominant bacteria of species Lactobacilli, as well as its effect However such considerations do not arise when considering the dermal surfaces of hands in the upper body, and thus it is expected that the formulations of many known art hand wash and/or body wash cleansing compositions are incompatible with the particular requirements of female intimate cleansing, particularly vaginal cleansing.

Thus, it is real and urgent need for improvements in feminine intimate cleansing compositions, as well as improved methods of cleansing of the vaginal region of the human female body, and methods for maintaining a good balance of naturally occurring bacterial flora incident to the vagina, during and/or after cleansing of the vaginal region of the human female body.

The foregoing needs, as well as further features and benefits of the present invention will become more apparent when considering the following specification.

In a first and preferred aspect of the present invention there is provided an acidic feminine intimate cleansing composition having a pH in the range of from 3.5 to 5, preferably from 4-4.5 inclusive, which necessarily comprises at least:

as a primary antimicrobial active constituent one or more of: lactic acid and/or a substituted lactic acid and/or a derivative thereof;
  and a ternary anionic constituent system which necessarily comprises one or more of each of: (a) a secondary alkane sulfonate compound(s), (b) an N-acyl sarcosinate compound(s), and (c) an aromatic hydrotrope compound(s), especially preferably is a cumene sulfonate compound, which ternary anionic constituent system boosts the antimicrobial efficacy of the primary antimicrobial active constituent present.

In a second embodiment there is provided an acidic feminine intimate cleansing composition having a pH in the range of from 3.5 to 5, preferably from 4-4.5 inclusive, which further necessarily comprises at least:

as a primary antimicrobial active constituent one or more of: lactic acid, and/or a substituted lactic acid and/or a derivative thereof;
  and a binary anionic constituent system which necessarily comprises one or more of each of: (a) a secondary alkane sulfonate compound(s), or (b) an N-acyl sarcosinate compound(s), and wherein only one of (a) or (b) is present with (c) an aromatic hydrotrope compound(s), which especially preferably is a cumene sulfonate compound, which binary anionic constituent system boosts the antimicrobial efficacy of the primary antimicrobial active constituent present.

According to a third embodiment, the present invention provides a feminine intimate cleansing composition according to the first or second embodiments which include further constituents which may provide additional technical and/or aesthetic attributes to the compositions, e.g., viscosity, cleansing, rinsing, pH adjusting agents, storage stability, etc. which attributes are frequently desired in consumer products.

In accordance with a fourth embodiment, the present invention provides a composition which demonstrates good antimicrobial efficacy against one or more of S. aureus, E. coli, C. albicans and/or K. pneumoniae.

According to a fifth embodiment, the present invention provides a method for the treatment of sensitive bodily tissues of the vaginal region of the female body, as well as the vagina itself, which method includes the step of: applying, (optionally repeatably applying) a therapeutically effective or an antimicrobially effective amount of a feminine intimate cleansing composition herein described to the vaginal region of the female body in order to provide a cleansing and/or antimicrobial benefit thereto.

In a further embodiment the present invention provides as a vendible article, a container which comprises a feminine intimate cleansing composition as herein described.

The foregoing as well as further aspects of the invention are described more fully in this patent specification.

As a first essential constituent, the inventive compositions comprise as a primary antimicrobial active constituent; lactic acid, and/or a substituted lactic acid and/or a derivative thereof, and as used herein expressly such encompass both the free acid form of lactic acid as well as salts or derivatives thereof which are preferred embodiments of the said first essential constituent. Nonlimiting examples of lactic acid and/or derivatives thereof include: lactic acid as well as alkyl lactates such as the reaction products of a $C_8$-$C20$ fatty alcohol with lactic acid. Preferred alkyl lactates include those represented by the following general structural formula (Ia):

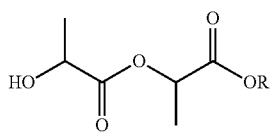

(Ia)

in which R is a $C_S$-$C20$ alkyl moiety, preferably is a $C_1$-$C_{14}$ alkyl moiety and especially preferably is predominantly (at least 85%, more preferably at least 90%, particularly preferably at least 95% and most preferably at least about 98%) of a $C_{12}$ alkyl moiety. The alkyl moiety may be branched but is preferably substantially linear. Further preferred alkyl lactates also include those which may be represented by the following general structural formula (Ib):

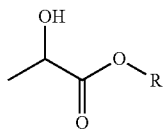

(Ib)

in which R is a $C_8$-$C_{18}$ alkyl moiety, preferably is a $C_{10}$-$C_{14}$ alkyl moiety and especially preferably is predominantly (at least 85%, more preferably at least 90%. particularly preferably at least 95% and most preferably at least about 98%) of a $C_{12}$ alkyl moiety. The alkyl moiety may be branched but is preferably substantially linear. Also useful are lactides as may be represented by the following formula (Ie):

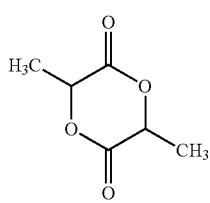

(Ie)

as well as polylactides as may be represented by the formula (Id):

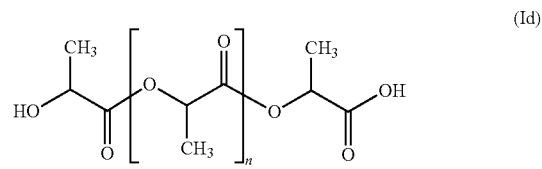

(Id)

wherein n is an integer of at least 1, preferably n is an integer from 1-100 inclusive, and particularly preferably n is 1-3. The lactic acid, salt or derivative may also be provided deposited upon an inorganic carrier such as silica. Of course it is to be understood that other alkyl lactates not specifically encompassed by the compounds of formulae (Ia), (1b), (Ie) and/or (Id) may also be utilized. The lactic acid and/or derivatives thereof may also be optionally substituted with one or more substituents, and by way of nonlimiting example, such substituents may be independently selected from alkyl, aryl, alcohol, ether, ester, cyanide, amide, amine, sulfate, phosphate, fluoro, chloro, bromo or iodo groups or carbonyl groups.

The lactic acid, and/or substituted lactic acid and/or a derivative thereof is necessarily present and comprises from about 0.01-5% wt., preferably from about 0.1-3% wt. of the inventive compositions. Alternately the lactic acid, and/or substituted lactic acid and/or a derivative is necessarily present in the topical compositions of the invention in an amount of from about 100 ppm/ml to about 50000 ppm/, more preferably from about 500 ppm/ml to about 30000 ppm, based on the volume of the feminine intimate cleansing composition of which it forms a part.

In addition to the foregoing first essential constituent, namely the primary antimicrobial active constituent, the feminine intimate cleansing compositions may in certain embodiments optionally additionally include an ancillary antimicrobial constituent which may be at least one organic acid compound which provides an antimicrobial effect. Such may be organic compounds which have less than about 12 carbon atoms, more preferably less than 10 carbon atoms and which comprise at least one moiety which impart acidity, preferably one or more groups selected from: most preferably are carboxyl groups (—COOH) which may provide a strong organic acid, and less preferably are hydroxyl groups (—OH), thiol group (—SH), enol groups (—C—C (OH)—), and phenols, which groups usually provide weaker organic acids than the preferred carboxyl groups (—COOH). The organic acid compounds may be aliphatic, aromatic, aryl, and may be substituted or unsubstituted with further functional groups. The foregoing moieties may be attached to any position of the carbon chain (or ring) of the antimicrobial constituent compound. Preferred are citric, ascorbic and benzoic acids, salts and/or derivatives thereof. It is to be further understood that one or more of these organic acids may also simultaneously function in adjusting the pH of the topical compositions of which they form a part. The compositions may also include one or more constituents which are effective in controlling and/or reducing fungi and/or yeasts, including those of the genus *Candida* and preferably *C. albicans*. However notwithstanding the foregoing, it is to be understood that one or more of the foregoing may be expressly excluded from the compositions of the invention. When present such may be included in effective amounts, and advantageously may be present in an amount of about 0.01-5% wt.

According to a first embodiment of the invention the feminine intimate cleansing compositions of the invention necessarily include a ternary anionic constituent system which comprises one or more of each of: (a) secondary alkane sulfonate compound(s), (b) N-acyl sarcosinate compound(s), and (c) aromatic hydrotrope compound(s), especially preferably which is a cumene sulfonate compound, which ternary anionic constituent system boosts the antimicrobial efficacy of the primary antimicrobial active constituent present, as compared to like compositions wherein the ternary anionic constituent system is absent.

According to a second embodiment, the feminine intimate cleansing compositions necessarily comprise a binary anionic constituent system which necessarily comprises one or more of each of: (a) a secondary alkane sulfonate compound(s), or (b) an N-acyl sarcosinate compound(s), and wherein only one of (a) or (b) is present with (c) an aromatic hydrotrope compound(s), especially preferably a cumene sulfonate compound, which binary anionic constituent system boosts the antimicrobial efficacy of the primary antimicrobial active constituent present, as compared to like compositions wherein the binary anionic constituent system is absent.

Each of the (a) a secondary alkane sulfonate compound(s), (b) N-acyl sarcosinate compound(s), and (c) aromatic hydrotrope compound(s) are described in more detail here.

The (a) secondary alkane sulfonate compound(s) are one or more compounds which include $C_1o$-$C_{24}$, preferably $CwC_{17}$ olefin sulfonate compounds of the general formula (A):

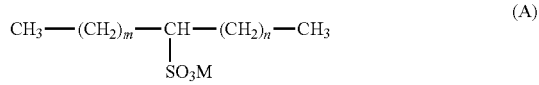

wherein m+n=an integer in the range of 7-21 inclusive, and is preferably an integer in the range of 11-14, inclusive, and M is a cation which is selected from an alkali metal such as sodium or potassium, an alkaline earth metal such as calcium or magnesium, ammonium, or an alkanolamine such as monoalkanolamine (e.g. monoethanolamine), dialkanolamine (e.g. diethanolamine), trialkanolamine (e.g. triethanolamine). However M is preferably sodium.

The (a) secondary alkane sulfonate may be symmetrically branched or may be asymmetrically branched. What is meant by the term "symmetrically branched" is that the sulfonate moiety branches from a carbon atom which is at the midpoint between the two terminal carbons of the alkane portion of the molecule, while the term "asymmetrically branched" is that the sulfonate moiety branches from a carbon which is not equidistant from the two terminal carbon atoms.

The (a) secondary alkane sulfonate(s) present in the compositions comprise from 0.25-6% wt., and are preferably present in an amount of 0.35-5% wt. Particularly preferred amounts, and preferred relative ratios, are disclosed with reference to one or more of the Examples set forth below.

The (b) N-acyl sarcosinate compound is a metal salt, preferably an alkali metal salt, of an N-alkyl-N-acyl amino acids. These are salts derived from the reaction of (I) N-alkyl substituted amino acids of the formula:

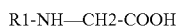

where $R_1$ is a linear or branched chain lower alkyl of from 1 to 4 carbon atoms, especially a methyl, for example, aminoacetic acids such as N-methylaminoacetic acid (i.e. N-methyl glycine or sarcosine), N-ethyl-aminoacetic acid, N-butylaminoacetic acid, etc., with (2) saturated natural or synthetic fatty acids having from 8 to 20 carbon atoms, especially from 10 to 14 carbon atoms, e.g. lauric acid, and the like.

The resultant reaction products are salts which may have the formula:

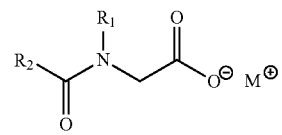

where M is an alkali metal ion such as sodium, potassium or lithium; $R_1$ is as defined above; and wherein $R_2$ represents a hydrocarbon chain, preferably a saturated hydrocarbon chain, having from about 6 to about 22 carbon atoms. Exemplary useful sarcosinate surfactants include cocoyl sarcosinate, lauroyl sarcosinate, myristoyl sarcosinate, palmitoyl sarcosinate, stearoyl sarcosinate and oleoyl sarcosinate, and tallow sarcosinate, of which preferred is the metal salts, preferably sodium salts, of lauroyl sarcosinate.

The N-acyl sarcosinate compound(s) present in the compositions comprise from 0.001-1% wt., and are preferably present in an amount of 0.01-0.35% wt. Particularly preferred amounts, and preferred relative ratios, are disclosed with reference to one or more of the Examples set forth below.

The feminine intimate cleansing compositions necessarily also comprise one or more anionic aromatic hydrotrope compounds, and preferably one or more aromatic hydrotrope compounds. Such include benzene sulfonate, naphthalene sulfonate, cumene sulfonate, xylene sulfonate and toluene sulfonate, as well as derivatives thereof such as $C_1$-$Cl_1$ alkyl benzene sulfonates. The anionic hydrotrope compounds are often provided in a salt form with a suitable counterion, such as one or more alkali, or alkali earth metals, such as sodium, calcium or potassium, especially sodium. However, other water soluble cations such as ammonium, mono-, di- and tri-lower alkyl, i.e. $C_{1-4}$ alkanol ammonium groups can be used in the place of the alkali metal cations. Specific, albeit non-limiting examples of anionic hydrotrope compounds include alkyl benzene sulfonates such as isopropylbenzene sulfonate, xylene sulfonates such as 2,3-xylene sulfonates, 2,4-xylene sulfonates, and 2,5-xylene sulfonates, toluene sulfonates such as a-toluene sulfonates, m-toluene sulfonates, and p-toluene sulfonates, cumene sulfonates, as well as mixtures thereof. Preferred anionic aromatic hydrotrope compounds are provided as salts, preferably as sodium salts and/or potassium salts. Of the anionic aromatic hydrotrope compounds, particularly preferred are salts of anionic aromatic hydrotrope compounds which comprise a sulfonate moiety, including compounds selected from the group consisting of: benzene sulfonate, naphthalene sulfonate, cumene sulfonate, xylene sulfonate and toluene sulfonate, and particularly preferably, compounds selected from: cumene sulfonate and/or xylene sulfonate.

The anionic aromatic hydrotrope compounds) present in the compositions comprise from 0.05-5% wt., and are preferably present in an amount of 0.075-3.5% wt. Particularly preferred amounts, and preferred relative ratios, are disclosed with reference to one or more of the Examples set forth below.

The inventors have surprisingly found that in the inventive embodiments which include the defined ternary anionic constituent system which necessarily comprises one or more of each of: (a) a secondary alkane sulfonate compound(s), (b) an N-acyl sarcosinate compound(s), and (c) an aromatic hydrotrope compound(s), that there are also preferred relative weight ratios of these (a), (b) and (c) anionic constituents. Preferably the relative parts by weight of (a):(b):(c) are in the range of: 0.5-4.5:0.025-0.25:1, more preferably in the range of 0.5-4:0.025-0.25:1. It is believed that in preferred ratios, wherein the (a) secondary alkane sulfonate compound(s) is present in excess of that of the (c) aromatic hydrotrope compound(s), and at the same time wherein the (b) N-acyl sarcosinate compound(s), are present in substantially lesser amounts, viz., at least about 75% lesser than the (c) aromatic hydrotrope compound(s), may be attributes in the increased antimicrobial efficacy against one or more bacteria selected from: S. aureus, E. coli, C. albicans, and K. pneumoniae demonstrated by the feminine intimate cleansing compositions.

With reference now to the second embodiment of the invention which includes the defined binary anionic constituent system which necessarily comprises one of: (a) a secondary alkane sulfonate compound(s), or (b) an N-acyl sarcosinate compound(s), but wherein only one of (a) or (b) is present, further with (c) an aromatic hydrotrope compound(s), that there are also preferred relative weight ratios of these (a), (b) and (c) anionic constituents. In a first binary anionic constituent system, (b) is absent from the composition and the relative parts by weight of (a):(c) are in the range of 0.5-4.5:1. In the second binary anionic constituent system, (a) is absent from the composition and the relative parts by weight of (b):(c) are in the range of 0.025-0.25:1. It is suspected that ratios, with respect to the required and absent compounds, may be attributes in the increased antimicrobial efficacy against certain bacteria as demonstrated by the feminine intimate cleansing compositions.

The feminine intimate cleansing composition necessarily comprises water, and preferably comprises at least 65% wt., preferably at least 75% wt. water. Concurrently however, the said compositions preferably comprises not more than 95% wt., more preferably not more than 90% wt. water. The water may be from any suitable source including available tap water such as from a municipal water supply, reservoir or well, as well as deionized, demineralized, or distilled water. Deionized, demineralized, or distilled water a particularly preferred as reducing the quantity of undesirable impurities which may be present The water is provided in quantum sufficient ("q.s.") in order to provide 100% wt. of the feminine intimate cleansing composition.

While not wishing to be bound by the following hypothesis it is nonetheless believed that by particular and required inclusion of the specific components of the anionic constituent system, whether a ternary such system as defined herein, or as either of the binary such systems as defined herein, impart to the compositions of the present invention an unexpected improvements in antimicrobial efficacy against various challenge organisms, and in particular against one or more of S. aureus, E. coli, C. albicans, and K. pneumoniae.

Again, while not wishing to be bound by the following, it is hypothesized that the selected specific components of the anionic constituent system operate in conjunction primary antimicrobial active constituent present potentiate the activity of the primary antimicrobial active constituent such that it may be used in relatively reduced amounts as compared to other and different systems known art compositions, which use different surfactants (and optionally further constituents as well, e.g. organic solvents) and/or different ratios of surfactants in order to achieve corresponding levels of antibacterial activity as demonstrated by the EN1276 test.

The feminine intimate cleansing compositions preferably exhibit at least a "3", preferably at least a "4" $Log_{10}$ reduction at contact times of 60 or 120 seconds of the bacteria selected from one or more of S. aureus, E. coli, C albicans, and K. pneumoniae when tested according to the demanding protocols of EN1276, and according to the "clean" conditions of the protocol. More preferred feminine intimate cleansing compositions of the invention exhibit at least a "4.5", preferably at least a "5" Log 10 reduction at contact times of 60 or 120 seconds according to the protocols of EN1276, and at contact times of 60 or 120 seconds according to that test protocol under "clean" conditions. Particularly preferred feminine intimate cleansing compositions exhibit at least a "3" $Log_{10}$ reduction at contact time at a 30 second contact time, and at least a "4" but preferably at least about a "5" $Log_{10}$ reduction at contact time of 60 seconds, according to the protocols of EN1276, and under "clean" or "dirty" conditions.

The feminine intimate cleansing compositions are acidic, and exhibit a pH in the range of from 3 to 5 inclusive, and in preferred embodiments exhibit a pH in the range of 4-4.75, inclusive. One or more acids and/or one or bases may be used as pH adjusting agents, or pH buffers, may be used to establish and/or maintain the pH of the feminine intimate cleansing compositions at a desired pH or within a desired pH range. Particularly preferred pH values are demonstrated with reference to one or more of the Examples.

The composition according to the invention may be formulated in numerous forms, including an aqueous or oily solution, or surfactant wash, as a dispersion or an emulsion or a gel. However, as previously noted, the compositions are preferably largely aqueous and are provided as either an aqueous or oily solution, or as a gel.

The feminine intimate cleansing compositions advantageously exhibit a viscosity at room temperature (20° C.-22° C.) of about 1-10,000 cP, preferably of about 200-5000 cP, and particularly preferably of about 500-3000 cPs. The viscosity my be determined by routine quantitative methods, such as by the use of a Brookfield RTV viscometer.

The feminine intimate cleansing compositions of the invention may include one or more further optional constituents which may be used to impart one or more desired technical and/or aesthetic attributes to the compositions. In certain preferred embodiments of the invention, one or more of the following recited optional constituents may be considered as essential constituents according to a particular preferred embodiment. Such optional constituents include additives and adjuvants which are conventional in the cosmetic, pharmaceutical or dermatological field, e.g., cosurfactants, hydrophilic or lipophilic gelling agents, hydrophilic or lipophilic active agents, further thickeners, hurnectants, opacifiers, preservatives, antioxidants, solvents especially organic solvents, pH adjusting agents, pH buffers, chelating agents, fragrances, materials which provide an aromatherapy benefit, fillers, dyestuffs or colorants, and light stabilizers including UV absorbers. When present, the total amount of these various additives and adjuvants are those conventionally used in the field, and, for example, range from 0.01% to 75%, preferably 0.01%-50% wt. of the total weight of the feminine intimate cleansing composition.

The inventive compositions may include one or more surfactants which may be any surface active agents, other than the (a) a secondary alkane sulfonate compound(s), (b) an N-acyl sarcosinate compound(s), and (c) an aromatic hydrotrope compound(s) previously described. Such include anionic, nonionic, amphoteric surfactants as well as cationic surfactants which are present in an amount and/or which do not undesirably interact with one or more anionic compounds which may be present, e.g. by forming undesired complexes therebetween which diminish the surface activity of either such anionic and cationic compounds.

Non-limiting examples of anionic surfactants include alcohol sulfates and sulfonates, alcohol phosphates and phosphonates, alkyl ester sulfates, alkyl diphenyl ether sulfonates, alkyl sulfates, alkyl ether sulfates, sulfate esters of an alkylphenoxy polyoxyethylene ethanol. alkyl monoglyceride sulfates, alkyl sulfonates, alkyl ether sulfates, alpha-olefin sulfonates, beta-alkoxy alkane sulfonates, alkyl ether sulfonates, ethoxylated alkyl sulfonates, alkylaryl sulfonates, alkylaryl sulfates, alkyl monoglyceride sulfonates, alkyl carboxylates, alkyl ether carboxylates, alkyl alkoxy carboxylates having 1 to 5 moles of ethylene oxide, alkylpolyglycolethersulfates (containing up to 10 moles of ethylene oxide), sulfosuccinates, octoxynol or nonoxynol phosphates, taurates, fatty taurides, fatty acid amide polyoxyethylene sulfates, acyl glycerol sulfonates, fatty oleyl glycerol sulfates, alkyl phenol ethylene oxide ether sulfates, paraffin sulfonates, alkyl phosphates, isethionates, N-acyl taurates, alkyl succinamates and sulfosuccinates, alkylpolysaccharide sulfates, alkylpolyglucoside sulfates, alkyl polyethoxy carboxylates, and mixtures thereof.

Further examples of anionic surfactants include water soluble salts or acids of the formula (ROS03)×M or (RS03)×M wherein R is preferably a $C_6$-$C_{24}$ hydrocarbyl, preferably an alkyl or hydroxyalkyl having a $C_{10}$-$C_{20}$ alkyl component, more preferably a $C_{12}$-$C_{15}$ alkyl or hydroxyalkyl, and M is H or a mono-, di- or tri-valent cation, e. g., an alkali metal cation (e. g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like) and x is an integer, preferably 1 to 3.

Further examples of anionic surfactants include alkyl-diphenyl-ethersulphonates and alkyl-carboxylates. Further anionic surfactants include salts (including, for example, sodium, potassium, ammonium, and substituted ammonium salts such as mono-, di- and triethanolamine salts) of soap, $C_6$-$C_{20}$ linear alkylbenzenesulfonates, $C_6$-$C_{22}$ primary or secondary alkanesulfonates, $C_6$-$C_{24}$ olefinsulfonates, sulfonated polycarboxylic acids prepared by sulfonation of the pyrolyzed product of alkaline earth metal citrates, $C_6$-$C_{24}$ alkylpolyglycolethersulfates (containing up to 10 moles of ethylene oxide); alkyl ester sulfates such as $C_{14}$-$J_6$ methyl ester sulfates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$-C18 monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula RO($CH_2CH_2$0) $kCH_2COO$-M+ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil.

One or more nonionic surfactants may also be present. Non-limiting examples of nonionic surfactants include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

Certain specific useful nonionic surfactants include primary and secondary linear and branched alcohol ethoxylates, such as those based on $C_6$-$C_{18}$ alcohols which further include an average of from 2 to 80 moles of ethoxylation per mol of alcohol. Examples include the Genapol® series of linear alcohol ethoxylates from Clariant Corp., Charlotte, N.C. The 26-L series is based on the formula RO($CH_2CH_2$0) nH wherein R is a mixture of linear, even carbon-number hydrocarbon chains ranging from $C_{12}H_{25}$ to $C_{16}H_{33}$ and n represents the number of repeating units and is a number of from 1 to about 12. Useful also are secondary $C_{12}$-$C_{15}$ alcohol ethoxylates, including those which have from about 3 to about 10 moles of ethoxylation. Such are available in the Tergitol® series of nonionic surfactants (DOW Chemical, Midland, Mich.).

More specific nonionic surfactants include those in which the major portion of the molecule is made up of block polymeric $C_2$-$C_4$ alkylene oxides, with alkylene oxide blocks containing $C_3$ to $C_4$ alkylene oxides. Such nonionic surfactants, while preferably built up from an alkylene oxide chain starting group, can have as a starting nucleus almost any active hydrogen containing group including, without limitation, amides, phenols, and secondary alcohols.

One group of nonionic surfactants containing characteristic alkylene oxide blocks are those which may be generally represented by the formula (A):

$$\text{HO-(EO)}x\text{(PO)}y\text{(EO)}_2\text{-H} \qquad (A)$$

where
EO represents ethylene oxide,
PO represents propylene oxide,
y equals at least 15,
(EO)x+z equals 20 to 50% of the total weight of said compounds, and,
the total molecular weight is preferably in the range of about 2000 to 15,000.

Another group of nonionic surfactants appropriate for use in the new compositions can be represented by the formula (B):

$$\text{R-(EO,PO)}a\text{(EO,PO)}b\text{-H} \qquad (B)$$

wherein
R is an alkyl, aryl or aralkyl group,
the alkoxy group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

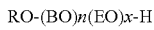
$$RO\text{-}(BO)n(EO)x\text{-}H \qquad (C)$$

wherein
R is an alkyl group containing 1 to 20 carbon atoms,
n is about 15 and x is about 15.

Also useful as the nonionic block copolymer surfactants which also include polymeric butoxy groups are those which may be represented by the following formula (D):

$$HO\text{-}(EO)x(BO)n(EO)y\text{-}H \qquad (D)$$

wherein
n is about 15,
x is about 15 and
y is about 15.

Still further useful nonionic block copolymer surfactants include ethoxylated derivatives of propoxylated ethylene diamine, which may be represented by the following formula:

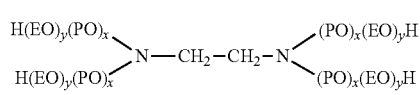

$$\begin{array}{c}H(EO)_y(PO)_x \\ H(EO)_y(PO)_x\end{array}\!\!\!>\!\!N\text{—}CH_2\text{—}CH_2\text{—}N\!\!<\!\!\!\begin{array}{c}(PO)_x(EO)_yH \\ (PO)_x(EO)_yH\end{array} \qquad (E)$$

where
(EO) represents ethoxy,
(PO) represents prop oxy,
the amount of (PO)x is such as to provide a molecular weight prior to ethoxylation of about 300 to 7500, and
the amount of (EO)y is such as to provide about 20% to 90% of the total weight of said compound.

Further useful nonionic surfactants include polyoxyethylene glycol ethers of $C_8$-$C_{24}$ fatty alcohols, such as steareth-2 and steareth-21, commercially available under the Brij tradename (ex. ICI).

Still further specific useful nonionic surfactants include alkyl glucosides, alkyl polyglucosides and mixtures thereof. Alkyl glucosides and alkyl polyglucosides can be broadly defined as condensation articles of long chain alcohols, e.g., $C_8$-$C_{30}$ alcohols, with sugars or starches or sugar or starch polymers i.e., glycosides or polyglycosides. These compounds can be represented by the formula (S)n-0-R wherein S is a sugar moiety such as glucose, fructose, mannose, and galactose; n is an integer of from about 1 to about 1000, and R is a $C_{8\text{-}30}$ alkyl group. Examples of long chain alcohols from which the alkyl group can be derived include decyl alcohol, cetyl alcohol, stearyl alcohol, lauryl alcohol, myristyl alcohol, oleyl alcohol and the like. Commercially available examples of these surfactants include decyl polyglucoside (available as APG 325 CS from Henkel) and lauryl polyglucoside (available as APG 600 CS and 625 CS from Henkel).

Certain preferred nonionic surfactants include fatty acid alkanolamides which are polyethylene glycol fatty acid amines (PEGylated alkanolamines), such as polyethylene glycol-4 fatty acid amines, a preferred embodiment of which is polyethylene glycol-4 rapeseedamide. Such are preferred as they may provide an improvement in foaming, and may also increase the viscosity of the compositions of which they form a part.

The feminine intimate cleansing compositions may comprise one or more amphoteric surfactants, nonlimiting examples of which include: alkylamine oxides, alkyamidopropyl amine oxides, alkyl betaines, alkyamidopropyl betaines, and sultaines. Specific examples of alkyl amine oxides that may be used in the present invention include octyl amine oxide, decyl amine oxide, lauryl amine oxide, iso-dodecyl amine oxide, myristyl amine oxide, cetyl amine oxide, oleamine oxide, stearyl amine oxide, and palmitamine oxide. Specific examples of alkylamidopropyl amine oxides that may be used in the present invention include laurylamidopropyl amine oxide, cocamidopropyl amine oxide, stearamidopropyl amine oxide, germamidopropyl amine oxide. Specific examples of alkyl betaines that may be used in the present invention include octyl betaine, lauryl betaine, cocobetaine, cetyl betaine, oleyl betaine, and tallow dihydroxyethyl glycinate. Specific examples of alkylamidopropyl betaines that may be used in the present invention include caprylamidopropyl betaine, capramidopropyl betaine, lauamidopropyl betaine, cocamidopropyl betaine, isostearamidopropyl betaine, wheatgermamidopropyl betaine, and coco/sunfloweramidopropyl betaine. Specific examples of sultaines that may be used in the present invention include cocamidopropyl hydroxysultaine and lauryl hydroxysultaine.

As an optional but preferred surfactant, the feminine intimate cleansing compositions may include a betaine surfactant which is, preferably selected from water dispersible and water soluble betaine surfactants. Exemplary betaine surfactants include those which may be represented by the general formula:

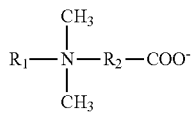

$$R_1\text{—}\underset{\underset{CH_3}{|}}{\overset{\overset{CH_3}{|}}{N}}\text{—}R_2\text{—}COO^-$$

wherein $R_1$ is an alkyl group containing from 8 to 18 carbon atoms, or the amido radical which may be represented by the following general formula:

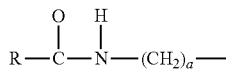

$$R\text{—}\underset{}{\overset{\overset{O}{\|}}{C}}\text{—}\underset{}{\overset{\overset{H}{|}}{N}}\text{—}(CH_2)_a\text{—}$$

wherein R is an alkyl group having from 8 to 18 carbon atoms, a is an integer having a value of from 1 to 4 inclusive, and $R_2$ is a $C_1$-$C_4$ alkylene group. Examples of such water-soluble betaine surfactants include dodecyl dimethyl betaine, cocoamidopropyl betaine as well as cocoamidopropyl dimethyl betaine, the latter of which is particularly preferred. In certain preferred embodiments, cocoamidopropyl dimethyl betaine is particularly preferred and in specific especially preferred embodiments is the sole betaine surfactant present in the inventive compositions. The identity of preferred betaine surfactants, and the preferred weights of the betaine surfactants are described with reference to one or more of the following examples. When preset, one or more such preferred betaine surfactants may be present in any effective amount, but are advantageously present in amounts of from 0.01-5% wt., and more preferably is from 1-3% wt.

However in certain embodiments one or more betaine surfactants may be expressly excluded.

A further optional but preferred surfactant which may present in the topical compositions are one or more amphoacetates such as sodium lauroamphoacetate, or diamphoacetates may also be used. Amphoacetates may be represented by the following general formula:

and, diamphoacetates may be represented by the following general formula:

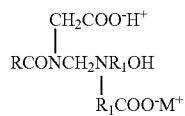

wherein in both formulas, R represents an aliphatic group having 8 to 18 carbon atoms, $R_1$ represents an aliphatic group having 1 to 5 carbon atoms, but is preferably —CHr, or —CH$_2$CHr, and M is a cation such as sodium, potassium, ammonium, or a substituted ammonium. Examples of such compounds include: sodium lauroamphoacetate, sodium cocoamphoacetate, disodioum lauroamphoacetate, and disodium cocoamphoacetate. The identity of preferred amphoacetates are disclosed with reference to the examples, and when present they may be in any effective amount. However, when present such one or more amphoacetates are preferably present in amounts of but are advantageously present in amounts of from 0.01-5% wt., and more preferably is from 0.5-3% wt. However in certain embodiments one or more said amphoacetates surfactants may be expressly excluded.

In certain preferred embodiments the compositions exclude cationic surfactants which independently provide an antimicrobial benefits such as cationic surfactants based on quaternary ammonium compounds, e.g, alkylbenzyl dimethyl ammonium chloride, and dialkyl dimethyl ammonium chloride.

The feminine intimate cleansing composition may comprise one or more humectants. Preferred humectants include sorbitol, hydroxypropyl sorbitol, erythritol, threitol, pentaerythritol, xylitol, glucitol, mannitol, hexylene glycol, butylene glycol (e.g., 1,3-butylene glycol), hexane trio! (e.g., 1,2,6-hexanetriol), glycerine, ethoxylated glycerine and propoxylated glycerine. Further useful humectants include sodium 2-pyrrolidone-5-carboxylate, guanidine; glycolic acid and glycolate salts (e.g. ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; and, panthenol. Still further humectants include polyols e.g., linear and branched chain alkyl polyhydroxyl compounds having a boiling point of at least 120° C., preferably at least 140° C. and yet more preferably at least 155° C. at 760 mm Hg(=1 atmosphere) such as: propylene glycoL polyethylene glycol, glycerine and sorbitol. Further exemplary hydrocarbons which may also serve as humectants are those having hydrocarbon chains anywhere from 12 to 30 carbon atoms, particularly, mineral oil, petroleum jelly, squalene and isoparaffins. Particularly preferred polyols useful as humectants are glycerine, glycerol, sorbitol as well as mixtures thereof. Glycerine and glycerol are particularly preferred for their use as humectants. When present such one or more humectants comprise about 0.01-20% wt. of the compositions of which it/they form a pmi. Especially referred humectants and preferred weights and/or weight ranges of humectants are described with reference to one or more of the following examples.

The feminine intimate cleansing compositions may comprise one or more chelating agents. Certain of these chelating agents may also provide a pH adjusting or pH buffering benefit as well. Exemplary useful chelating agents include those known to the art, including by way of non-limiting example; aminopolycarboxylic acids and salts thereof wherein the amino nitrogen has attached thereto two or more substituent groups. Useful chelating agents include one or more of ethylene diamine tetra acetic acid (EDTA), diethylene triamine penta acetic acid (DTPA), ethane-I-hydroxy-1,1-diphosphonate (EHDP), ethylene diamine-N,N'-disuccinate (EDDS), nitrilo triacetic Acid (NTA), sodium imino disuccinate (IDS), ethylene glycol-bis-(2-aminoethyl)-N,N,N',N'-tetra acetic acid (EGTA), methyl glycine diacetic acid (MGDA), N-(2-hydroxyethyl) ethylene diamine N,N',N'-thacetic acid) (HEDTA), ethylene diamine tetra methylene phosphonic acid (EDTMP), diethylene thamine-penta-methylene phosphonic acid (DTPMP), glutamic acid-N,N-diacetic acid (GLDA), cyclohexane-1,2-diamine-N,N,N',N'-tetra-acetic acid (CDTA), 1,3-propylenediamine tetra acetic Acid (PDTA), ethylene diamine triacetic acid (EDTA), L-hydroxy imino disuccinic acid (L-IDS), trisodium N-carboxyethyl imino succinate (CEIS), sodium tripolyphosphate (STP), thethylene tetramine hexaacetic acid (TTHA). Other preferred chelating agents are succinates, e.g., trisodium ethylene diamine disuccinate, tetra-sodium imino disuccinate, glutamic acid-N,N diacetic acid tetra sodium salt, 2-hydroxyethyl iminodiacetic acid, sodium salt (disodium ethanol diglycinate), tetrasodium 3-hydroxy-2,2 imino disuccinate, trisodium methylglycine diacetic acid, L-aspartate-N,N-diacetic acid tetrasodium salt. Particularly preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used. Such particularly preferred chelating agents are highly effective, available at low-cost, and are generally mild to the skin, hair and other topical surfaces. Nonlimiting examples of commercially available chelating agents include those marketed under the "Dissolvine" trademark (ex. AkzoNobel). When present such one or more chelating agents usually comprise from 0.001-1% wt. of the inventive compositions.

The feminine intimate cleansing compositions may also comprise one or more further topically active ingredients useful in skincare, preferably one or more active ingredients which are effective in reducing or eradicating yeasts and/or fungi which may be present, e.g., organisms of the genus *Candida*, and in particular *Candida albicans*. Nonlimiting examples of such topically active ingredients include one or more of the following: further antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin;

antiviral compounds, for example selected from acyclovir, tamvir, and penciclovir; antifungal compounds, for example selected from the following: farnesol, clotrimazole, ketoconazole, econazole, fluconazole, calcium or zinc undecylenate, undecylenic acid, butenafine hydrochloride, ciclopirox olairnine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc; as well as anthelmintic compounds, for example metronidazole. When present any one or more such further topically active ingredients may be present in a therapeutically effective amount, which may vary upon the identity of the further topically active ingredient used.

The feminine intimate cleansing compositions may optionally include one or more thickeners which are not found to deleteriously affect the favorable technical characteristics of the present invention, especially the antimicrobial characteristics. Coming into consideration are one or more of polysaccharide polymers selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum. tragacanth gum, sclerotium gum or derivatives thereof, polycarboxylate polymers, polyacrylamides, polyacrylate cross-polymer thickeners, clays, and mixtures thereof.

When the feminine intimate cleansing compositions are provided as gels, while such may be aqueous or non-aqueous, due to the high water content of the said compositions, aqueous gels are preferred. Such a gel will contain one or more gelling agents in order to impart sufficient viscosity to the gel. Suitable gelling agents may be thickners based on gums or derivates thereof such as hydroxypropyl guar or may be a copolymer of acryloyl dimethyl tauric acid (or a salt thereof), especially a copolymer of that monomer with another vinylic monomer. The salt may be a salt of a Group I alkali metal, but is more preferably an ammonium salt. Examples of suitable copolymer gelling agents are ammonium acryloyl dimethyl taurate/vinyl pyrrolidone copolymer, ammonium acryloyl dimethyl taurate/Beheneth-25 methacrylate copolymer, ammonium acryloyldimethyltaurate/vinyl formamide copolymer These materials are available from Clariant GmbH in the range of products under the trade name Aristoflex.

When present, the amount of gelling and/or thickening agent in the feminine intimate cleansing composition preferably lie in the range 0.05-10% wt., more preferably 0.5-5% wt. but preferably (and in order of increasing preference) the amount of gelling and/or thickening agent is not in excess of 4.5% wt/, 4% wt., 3.5% wt., 3% wt., 2.5% wt., 2% wt., 1.75% wt., 1.5% wt., 1.25% wt., 1.0% wt.

As previously noted, the feminine intimate cleansing compositions may take the form of largely aqueous composition, or may be provided as an oily solution, as a surfactant wash, as a foam, as a dispersion, an emulsion or as a gel. An emulsion may be an oil-in-water emulsion or a water-in-oil emulsion or a microemulsion. By way of non-limiting examples, the oil phase of emulsions may comprise: hydrocarbon oils such as paraffin or mineral oils; waxes such as beeswax or paraffin wax; natural oils such as may be derived from plants, such as sunflower oil, apricot kernel oil, shea butter or jojoba oil; silicone oils such as dimethicone, cyclomethicone or cetyldimethicone; fatty acid esters such as isopropyl palmitate, isopropyl myristate, dioctylmaleate, glyceryl oleate and cetostearyl isononanoate; fatty alcohols such as cetyl alcohol or stearyl alcohol and mixtures thereof (eg cetearyl alcohol); polypropylene glycol or polyethylene glycol ethers, eg PPG-14 butyl ether; as well as mixtures of any of the foregoing.

Emulsifiers used may be any emulsifiers known in the art for use in water-in-oil or oil-in-water emulsions or microemulsions. Known cosmetically acceptable emulsifiers may include: sesquioleates such as sorbitan sesquioleate, available commercially for example under the trade name Arlacel 83 (ex. ICI), or polyglyceryl-2-sesquioleate; ethoxylated esters of derivatives of natural oils such as the polyethoxylated ester of hydrogenated castor oil available commercially for example under the trade name Arlacel 989 (ex. ICI); silicone emulsifiers such as silicone polyols available commercially for example under the trade name ABIL WS08 (ex. Th. Goldschmidt AG); anionic emulsifiers such as fatty acid soaps e.g. potassium stearate and fatty acid sulphates, e.g. sodium cetostearyl sulphate available commercially under the trade name Dehydag (ex. Henkel); ethoxylated fatty alcohols, for example the emulsifiers available commercially under the trade name Brij (ex. ICI); sorbitan esters, for example the emulsifiers available commercially under the trade name Span (ex. ICI); ethoxylated sorbitan esters, for example the emulsifiers available commercially under the trade name Tween (ex. ICI); ethoxylated fatty acid esters such as ethoxylated stearates, glyceryl monostearates for example the emulsifiers available commercially under the trade name Myrj (ex. ICI); ethoxylated mono-, di-, and tri-glycerides, for example the emulsifiers available commercially under the trade name Labrafil (ex. Alfa Chern.); non-ionic self-emulsifying waxes, for example the wax available commercially under the trade name Polawax (ex. Croda); ethoxylated fatty acids, for example, the emulsifiers available commercially under the trade name Tefose (ex. Alfa Chern.); methylglucose esters such as polyglycerol-3 methyl glucose distearate available commercially under the name Tegocare 450 (ex. Degussa Goldschmidt); polyacrylamide emulsifier systems for examples cream gel emulsifier under trade name Sepigel 305 (ex. Seppic); as well as mixtures thereof.

The feminine intimate cleansing compositions may include a cosmetic particulate material, which may be any particulate material which is a solid at room temperature, which does not deleteriously react chemically with the balance of the constituents of the inventive composition. Advantageously the cosmetic particulate is insoluble in balance of the constituents of the feminine intimate cleansing compositions. Such cosmetic particulate materials may beneficially provide for a controlled and desirably degree of skin abrasion when the feminine intimate cleansing composition is applied, and especially where it is rubbed into the skin.

Exemplary materials useful for the cosmetic particulate material include: inorganic particulates, polymeric organic particulates, carbonates, hollow silica microspheres, glass microcapsules, ceramic microcapsules, inorganic pigments, crystalline and microcrystalline waxes derived from plants, mineral oils or petroleum, hollow polymer microspheres, starches, alginates, organic dyestuffs or pigments, and mixtures thereof. Mixtures of two or more cosmetic particles may be used to provide the cosmetic particulate constituent. Preferred as the cosmetic particulate constituent are materials which provide an exfoliating benefit. A preferred class of cosmetic particulate materials are those based on synthetically occurring or synthetic waxes inclusive of microcrystalline waxes. Preferred cosmetic particulates are those having an average particle size in the range of about 1-100 microns, more preferably about 5-50 microns, as measured along the widest dimension of the particulate. When included in the compositions of the invention, the cosmetic particulate constituent of the invention may be provided in any effective amount, advantageously from at least 0.01% wt., preferably at least 0.05% wt, and most preferably at least 0.1% wt of the feminine intimate cleansing composition. Similarly advantageously the cosmetic particulate constituent is present in not more than 10% wt., preferably not more than 5% wt, and yet more preferably not more than 2% wt, and most preferably not more than 2% wt of the feminine intimate cleansing composition of which it forms a part.

The feminine intimate cleansing compositions may also a cationic Polyquarternium-type polymer. Such materials are well known to the art of topical compositions and are described in the literature, particularly in the International Cosmetic Ingredient Dictionary and Handbook, Volume 2 ($9^1$h Edition, 2002), at pages 1311-1319. Other polyquarternium compounds although not specifically elucidated here may also be utilized in the present inventive compositions. When present, the one or more cationic polyquarternium-type polymers are advantageously present in amounts of from about from 0.001-5% wt., preferably in amounts from 0.01 λ% wt., but are most desirably present in reduced weight percentages from about 0.05-1% wt. based on the total weight of the feminine intimate cleansing composition of which they form a part.

A further optional constituent which may be included in the feminine intimate cleansing compositions is a latex. Such are used to provide opacification of the composition, and are also referred to in the art as "opacifiers". Such are materials which are typically emulsions, dispersions or suspensions of a water insoluble polymer or copolymer in an carrier. The carrier may be aqueous, an aqeuous/organic solvent mixture or organic solvent. The latex may be based on a homopolymer, or on copolymer formed from styrene, alpha-methylstyrene, divinylbenzene, acrylic acid or $C_1$-$C_{20}$ esters thereof, methacrylic acid or $C_1$-$C_{20}$ esters thereof, (meth)acrylamide, maleic acid, vinyl acetate, crotonic acid, vinyl neodecanoate and butenoic acid.

Particularly preferred latexes useful in the present invention are latexes presently commercially available under the trademark ACUSOL (ex. Rohm & Haas Inc.). When present in a composition, the latex may be present in amounts of up to about 5% wt., preferably are present in amounts of from about 0.001% wt. to about 3% wt., preferably are present in amount from about 0.1% wt. to about 1.2% wt, and most preferably are present in amounts of from about 0.1% wt. to about 1% wt., based on the total weight of the topical composition of which it forms a part. Concurrently the amount of the of the water-insoluble polymer present in the latex may range from about 0.01 to about 90%, preferably from about 0.1 to about 60%, optimally from about 10 to about 50% by weight of the latex.

The feminine intimate cleansing compositions may include one or more preservatives. Such may include, for example one or more compounds such as: phenoxyethanol, ethylhexylglycerin, dicaprylyl glycol, formaldehyde solutions, parabens, pentanediols, benzoic acid, sorbic acid, benzyl alcohol, as well as mixtures of two or more of the foregoing. Non-limiting examples of commercially available preservative preparations include a mixture of 5-chloro-2-methyl-4-isothiazolin-3-one and 2-methyl-4-isothiazolin-3-one marketed under the trademark KATHON CG/ICP as a preservative composition (ex. Rohm and Haas Inc.), and a mixture of mixture of caprylyl glycol and ethylhexylglycerin supplied as Sensivia SC10 (ex. Schiilke +Mayr). Further useful preservative compositions include KATHON CG/ICP II (ex. Rohm and Haas Inc.), PROXEL (ex. Zeneca), SUTTOCIDE A (ex. Sutton Laboratories) as well as TEXTAMER 38AD (ex. Calgon Corp.) Preferred preservative compositions are based on one or more constituents which are considered to be "natural" or "organic" materials by relevant standards setting organizations (e.g., ECOCERT, NaTrue, BDIH) such as blends of benzyl alcohol, benzoic acid and sorbic acid which in even very low concentration (about 1% wt. or less) provide a long term product preservative effect. When present the preservative is included in any amount found to be effective in retarding or inhibiting the grown of undesired microorganisms in the feminine intimate cleansing compositions, particularly during storage for several months at room temperature. When present in a composition, in accordance with certain of the preferred embodiments, the preservative composition is advantageously present in amounts of up to about 1.5% wt., preferably are present in amounts of from about 0.00001% wt. to about 1% wt., based on the total weight of the composition of which it forms a part.

The feminine intimate cleansing compositions may include one or more organic solvents. By way of non-limiting example exemplary useful organic solvents include those which are at least partially water-miscible such as low molecular weight alcohols, such as, $C_1$-$C_6$ monohydric alcohols including, e.g. ethanol, propanol, isopropanol, and butanol; glycols, e.g., ethylene glycol, propylene glycol, hexylene glycol; water-miscible ethers, e.g. diethylene glycol diethylether, diethylene glycol dimethylether, propylene glycol dimethylether; water-miscible glycol ethers, e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether; lower esters of monoalkylethers of ethylene glycol or propylene glycol, e.g. propylene glycol monomethyl ether acetate, and mixtures thereof. Glycol ethers having the general structure Ra—Rb—OH, wherein Ra is an alkoxy of 1 to 20 carbon atoms, or aryloxy of at least 6 carbon atoms, and Rb is an ether condensate of propylene glycol and/or ethylene glycol having from one to ten glycol monomer units are also useful. When present they may be used in any effective amount, and advantageously are present from 0.01% wt., to about 5% wt. of the inventive compositions.

The feminine intimate cleansing compositions may optionally include a fragrance constituent, which may be based on natural and/or synthetic fragrances and most commonly are mixtures or blends of a plurality of such fragrances, optionally in conjunction with a carrier such as an organic solvent or a mixture of organic solvents in which the fragrances are dissolved, suspended or dispersed. Such may be natural fragrances, e.g, natural extracts of plants, fruits, roots, stems, leaves, wood extracts, e.g. terpineols, resins, balsams, animal raw materials, e.g., civet and beaver, as well as typical synthetic perfume compounds which are frequently products of the ester, ether, aldehyde, ketone, alcohol and hydrocarbon type, e.g., benzyl acetate, linalyl acetate, citral, citronella!, methyl cedryl ketone, eugenol, isoeugenol, geraniol, linalool, and Typically it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. When present the fragrance constituent may be present in any effective amount such that it can be discerned by a consumer of the composition, however such is advantageously present in amounts of up to about 1% wt., preferably in amounts of from about 0.00001% wt. to about 0.5% wt., and most preferably in an amount of from about 0.0001% wt. to 0.5% wt. based on the total weight of the composition of which it forms a part.

The feminine intimate cleansing compositions of the invention may optionally further comprise one or more botanical extracts. Such may provide an "aromatherapy benefit". Such are to be understood to be in addition to any fragrance or perfume constituent which might also be concurrently present, or one or more of such botanical extracts may also provide a fragrancing benefit as well. Nonlimiting examples of suitable botanical extracts include one or more extracts from plants (herbs, roots, flowers, fruits, seeds) such as flowers, fruits, vegetables, and so on, including acacia (dealbata, farnesiana, senegal), acer saccharinum (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, green tea, chamomile, willowbark, mulberry, poppy, and the like. Further botanical extracts include one or more essential oils, including one or more of: Bergamot—*Citrus aurantium bergamia* (Bergamot) Fruit Oil, Coconut—*Cocos nucifera* (Coconut) Oil, Basil—*Ocimum basilicum* (Basil) Oil, Tangerine—*Citrus nobilis* (Mandarin Orange) Peel Oil, Geranium—*Pelargonium graveolens* Flower OiL Jasmine—*Jasminum officinale* (Jasmine) Oil, Lavender—*Lavandula angustifolis* (Lavender) Oil, Lemon—*Citrus medica limonum* (Lemon) Peel Oil, Lime—*Citrus aurantium dulcis* (Orange) Peel Oil, Clove—*Eugenia caryophyllus* (Clove) Leaf Oil, Spearmint—*Mentha viridis* (Spearmint) Leaf Oil, Vanilla—*Vanilla planifolia* Fruit Extract, Patchouli—*Pogostemon cablin* Oil, Curry Leaf—*Murraya koenigii* (Curry) Leaf Oil, Cinnamon Leaf—*Cinnamomum cassia* Leaf Oil, Chamomile–*Anthemis nobilis* Flower Oil, Orange—*Citrus aurantium dulcis* (Orange) Peel Oil, Clary Sage—*Salvia sclarea* (Chffy) Oil, Tea Tree—*Melaleuca alternifolia* (Tea Tree) Leaf Oil. Further botanical extracts include terpenes, terpene alcohols, sesquiterpene alcohols, terpinen-4-ol, bisabolol, farnesol, anise oils, neroli, sandalwood, geraniol, neral, citronellal, chamomile extracts, lemongrass oil, linalool, eugenol, carvacrol, thymol, and cinnamaldehyde. When present, such botanical extracts may be present in any effective amount but advantageously are present in an amount of at least about 0.001% wt., preferably from about 0.01% wt.-7.5% wt. based on the total weight of the composition of which it forms a part. It is to be understood that these one or more botanical extracts may be used with our without the optional fragrancing constituent recited previously and may be used wholly or partially in place of said fragrancing constituent.

The inventive feminine intimate cleansing compositions may include one or more colorants, e.g, dyes or pigments which are known to the art be useful in cosmetic or topical compositions which may be used to impart a desired color or tint to the inventive compositions. Any colorant which is compatible with the other constituents forming the topical compositions may be used and such may be present in any amount effective to achieved the desired visual effect. Preferred are pigments and/or dyes approved for use in topical compositions by an appropriate government body or agency, such as FD&C dyes used in the U.S.A. Advantageously one or more colorants may be added in amounts of about 0.001% wt. to about 0.1% by weight, based on the total weight of the composition of which the colorant(s) forms a part.

The compositions may optionally include one or more vitamins, vitamin derivatives and/or vitamin precursors, nonlimiting examples of which include Vitamin A. D, E, panthenol, niacinamide, and retinyl palmitate. When included, such one or more such vitamins, derivatives and/or precursors thereof may be present in a therapeutically effective amount, which may vary upon the identity of the particular such material. Advantageously, amounts of from 0.0001-lo/owt., preferably from 0.001-0.75% wt. based on the total weight of the feminine intimate cleansing compositions are expected to be effective.

The feminine intimate cleansing compositions may include one or more antioxidant constituents. Examples of antioxidants include but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, glutathione, and ascorbic acid and ascorbic acid derivatives (e.g., ascorbyl palmitate and ascorbyl polypeptide). Oil-soluble antioxidants suitable for use in the feminine intimate cleansing compositions of this invention include, but are not limited to, butylated hydroxytoluene, retinoids, tocopherols e.g., tocopherol acetate, tocotrienols, and ubiquinone. Natural extracts containing antioxidants suitable for use in the topical compositions of this invention, include but not limited to, extracts containing flavonoids and isoflavonoids and their derivatives, extracts containing resveratrol and the like. Examples of such natural extracts include grape seed, green tea, pine bark, propolis, and the like. When present the total amount of such antioxidants are usually not in excess of 5% wt, preferably are present in amounts of from 0.0001-4% wt. based on the total weight of the feminine intimate cleansing compositions of which it forms a part. In certain preferred embodiments one or more antioxidants constituents are necessarily present.

The feminine intimate cleansing compositions may include one or more light stabilizers and/or UV absorbers. Such materials are known to be useful in cosmetic or topical compositions and impart a degree of stability to the compositions which may comprise one or more components which may be deleteriously affected when exposed to certain sources of light, e.g., sunlight. Other such materials are known to stabilize or improve the effect of colorants which may be present in the compositions. Any cosmetically acceptable material or compound which provides protection for one or more of the constituents in the inventive compositions from photolytic degradation or photo-oxidative degradation may be used. Exemplary and preferred such materials which are presently commercially available include one or more of: CIBAFAST H liquid, described to be sodium benzotriazolyl butylphenol sulfonate with Buteth-3 and tributyl citrate; TINOGARD HS described to be sodium benzotriazolyl butylphenol sulfonates; TINOGARD AS described to be bumetrizole; TINOGARD TL described to be benzotriazolyl dodecyl p-cresol; and TINOGARD Q described to be tris(tetramethyl-hydroxypiperidinol) citrate, all of which are presently commercially available from Ciba Specialty Chemicals (Muttenz, CH.). When present, the one or more light stabilizers as well as UV absorbers may be included in any effective amount; advantageously such materials are present in amounts of from 0.0001-1% wt., preferably from 0.001-0.5% wt. based on the total weight of the feminine intimate cleansing composition of which it forms a part.

In certain preferred embodiments sodium octane sulfonates are excluded from the inventive compositions.

The amount or dose (e.g, mass and/or volume) of the feminine intimate cleansing compositions which is to be applied to the skin depends in great part upon (a) the specific composition and its included constituents, and (b) the desired degree cleansing desired. Further, it is to be understood that ultimately that after one or more applications with a certain amount of applied feminine intimate cleansing compositions the desired effect cannot be achieved, then a greater amount of the composition can be used and applied to the vaginal region, e.g. by applying more of the topical composition at a single application, and/or by a more frequent regimen of application of the cleansing composition. Effective concentrations a/o effective treatment amounts applied a/o effective frequency of application (treatment regimen) may be easily determined by the user of the said cleansing composition.

The feminine intimate cleansing compositions may be used as a liquid. a foam or or a gel type product and be directly applied, e.g. such as by the user's hands to a topical surface, e.g, topical surfaces of the female body and in particular the region of the groin. The feminine intimate cleansing compositions may be dispensed from a carrier substrate, which may be an applicator pad or wipe. Useful wipes include fibrous materials formed of natural and/or synthetic fibers may be used. Such may be woven or nonwown to form a fabric or sheet used as the wipe, or as a pad. The nonwoven fabrics may be a combination of wood pulp fibers and textile length synthetic fibers formed by well known dry-form or wet-lay processes. Synthetic fibers such as rayon, nylon, orlon and polyester as well as blends thereof can be employed. Such fibers can be resin bonded, hydroentangled, thermally bonded, meltblown, needlepunched, or any combination of the former. The substrate of the wipe may also be a film forming material such as a water soluble polymer. Also useful as carrier substrates are closed cell, or open celled foams such as polyurethane foams as well as regenerated cellulose foams, which may also be referred to as sponges. The preimpregnated pads or wipes may be provided at any use loading ratio of treatment composition: non-impregnated pad or wipe, but preferably such are loading ratio is the range of about 0.1-5 w/w, preferably 0.5-5:1 w/w.

Dry preimpregnated pads or wipes can mean made by simply applying a suitable amount of the feminine intimate cleansing composition, and thereafter allowing it to dry, in which case the initial loading ratio prior to any drawing is considered as being effective loading ratio of treatment composition: non-impregnated pad or wipe.

In use, a quantity of the feminine intimate cleansing composition may be first applied by consumer onto a carrier substrate and thereafter the carrier substrate is used to deliver the composition to a topical surface. Alternately, a carrier substrate may be supplied in a preimpregnated form with a quantity of the feminine intimate cleansing composition such that in use the consumer may dispense one or more preimpregnated carrier substrates, viz., wipes, pads or sponges, from a container or package and thereafter deliver the feminine intimate cleansing compositions by contacting the preimpregnated carrier substrate to the skin or tissues. Such a preimpregnated applicator pad or wipe may be supplied in a wet state, where it is ready to use and can be directly applied to a topical surface, or alternatively it may be applied in a dry state where it is required to be wetted with water prior to, or during its use and application onto a topical surface.

The feminine intimate cleansing compositions may be packaged in any suitable container for storage and/or dispensing as may be desired or required. Such include non-pressurized containers such as jars, non-deformable (e.g., glass) and deformable (e.g., polymeric) tube, flasks or bottles. When formulated as a foaming liquid composition, the feminine intimate cleansing compositions are preferably supplied in a manually pumpable dispenser which facilitates the formation of a foam from the liquid. Nonlimiting examples of such dispensers include those disclosed in one or more of U.S. Pat. Nos. 5,271,530, 6,840,408, and 7,461,762. The inventive compositions may be dispensed directly from a container by simply scooping a quantity from, or by pouring a quantity of the topical composition from the open end of ajar, flask or bottle, each of which are desirably resealable by the added provision of a removable cap, cover, plug, flow dispensing cap (e.g., a cap with a flip up cover obscuring a dispensing orifice) or nozzle (e.g., a cap with a push-pull element, or a flip-up element which defines a flow path for the composition as it exits the container). Such a non-pressurized container may also further include a manually operable pump a part of which may be moved or compressed in order to dispense a quantity of the treatment composition from within the container.

When the feminine intimate cleansing composition is supplied as a product in the form of a preimpregnated pad or wipe, (which may be wet or dry) the product may be supplied in any suitable container for storage and/or dispensing which maybe is a dispense a single, or a plurality of preimpregnated pads or wipes. Single preimpregnated pads or wipes are conveniently provided in breachable envelopes or pouches formed from barrier materials, such as polymeric films, foils, and metallized polymer films, and/or, co-laminates of one or more of the foregoing such barrier materials. Such barrier materials aid in retaining the moisture content of the preimpregnated pad or wipe prior to use. A plurality of preimpregnated pads or wipes a be provided in a sealable container which may be used to dispense one or more pads or wipes as desired, and thereafter closed by consumer or user. Examples include polymeric tubs, flasks, and resealable pouches.

The feminine intimate cleansing composition may also be provided in container, viz, a supply container or refill container which is designed for use in conjunction with further apparatus which is used to dispense quantities of the said composition. Such include, for example devices which include a motor-driven pump, which is operable in response to an input from the device and/or the consumer which causes the pump to operate and dispense the topical composition through a flowpath which extends from the said container to a delivery port or nozzle through which the treatment composition exits the apparatus. Non-limiting, albeit preferred apparatus include those disclosed in one or more of: US 20130206789 A1, US 20120097711 A1, and WO/2010/055314.

The feminine intimate cleansing composition may also be provided in pressurized or pressurizable container, e.g., an aerosol canister supplied with a conventional valve through which quantities of the feminine intimate cleansing composition may be dispensed. In such an embodiment the compositions of the invention would additionally require a propellant, which may be chosen from those presently used in the art and include, for example, compressed gases such as carbon dioxide, compressed air, or nitrogen, as well as $C_1$-$C_{10}$ hydrocarbons, such as n-propane, n-butane, isobutane, n-pentane, isopentane, dimethyl ether and blends thereof may be used. When utilized, an amount of about 0.5-25% wt. of propellant is added to a 100% wt. feminine intimate cleansing composition previously formed.

The feminine intimate cleansing compositions may be used as a remedial or therapeutic treatment and/or as a prophylactic treatment for maintaining cleanliness of the groin area, and in particular the vaginal region of the groin area of human females.

The following examples below illustrate exemplary formulations as well as preferred embodiments of feminine intimate cleansing compositions according to the invention. It is to be understood that these examples are provided by way of illustration only and that further useful formulations falling within the scope of the present invention and the claims may be readily produced by one skilled in the art without deviating from the scope and spirit of the invention.

EXAMPLES

A number of feminine intimate cleansing compositions according to the present invention are disclosed with reference to Tables IA and IB. Compositions according to the invention are identified by the use of the letter "E" prefixing one or more further numerals a/o letters, while comparative compositions are identified by the letter "C" prefixing one or more further numerals a/or letters.

The formulation(s) of Table IA were produced and tested, the formulations of Table IB represent formulae which may be produced. In the compositions reported on Table 1A and 1B, the identified compounds/constituents were supplied by raw materials identified on Table 2 which may have had less than 100% wt. or were 100% wt. "active" of the named compound/constituent, however it is to be understood that the amounts of each identified compound a/o constituent is reported on Table 1 as being "100% wt. active" basis. Additionally, to each of the compositions was included deionized water in "quantum sufficient" (q.s.) in order to provide 100 parts by weight of the specific composition, and in some instances an amount of one or more pH adjusting constituents, e.g., acids and/or bases, such as sodium hydroxide, may have been added in order to establish a desired pH for the composition, which similarly required a "q.s." amount.

TABLE 1A

|  | E1 |
| --- | --- |
| sodium secondary alkane sultanate (60%) | 6.66 |
| sodium lauroyl sarcosinate (30%) | 0.70 |
| sodium cumene sultanate (40%) | 2.50 |
| sodium lauryl ether sulfate 2EO (70%) | 6.44 |
| cocoamidopropyl betaine (30%) | 2.25 |
| lactic acid (90%) | 2.50 |
| PEG-4 rapeseedamide (95%) | 0.90 |
| NaOH (aq. soln.) (30%) | 0.10 |

TABLE 1A-continued

|  | E1 |
| --- | --- |
| sodium chloride | 5.00 |
| tetrasodium glutamate diacetate (47%) | 0.20 |
| preservative1 | 1.00 |
| fragrance | 0.25 |
| d.i. water | q.s. |
| pH | 4.19 |

TABLE 1B

|  | E2 | E3 | E4 | E5 | E6 |
| --- | --- | --- | --- | --- | --- |
| sodium secondary alkane sulfonate (60%) | 6.66 | 2.5 | — | 6.66 | 6.66 |
| sodium lauroyl sarcosinate (30%) | 0.7 | 0.7 | 0.7 | 0.22 | — |
| sodium cumene sulfonate (40%) | 2.5 | 2.5 | 2.5 | 2.5 | 2.5 |
| sodium lauryl ether sulfate 2EO (70%) | 6.44 | 6.44 | 6.44 | 6.44 | 6.44 |
| cocoamidopropyl betaine (30%) | 2.25 | 2.25 | 2.25 | 2.25 | 2.25 |
| lactic acid (90%) | 2.5 | 2.5 | 2.5 | 2.5 | 2.50 |
| PEG-4 rapeseedamide (95%) | 0.9 | 0.9 | 0.9 | 0.9 | 0.90 |
| glycerine | 5.0 | 5.0 | 5.0 | 5.0 | 5.0 |
| NaOH (aq. soln.) (30%) | 0.1 | 0.1 | 0.1 | 0.1 | 0.10 |
| sodium chloride | 2.0 | 2.0 | 2.0 | 2.0 | 2.0 |
| tetrasodium glutamate diacetate (47%) | 0.2 | 0.2 | 0.2 | 0.2 | 0.2 |
| preservative2 | 0.9 | 0.9 | 0.9 | 0.9 | 0.9 |
| fragrance | 0.1 | 0.1 | 0.1 | 0.1 | 0.1 |
| d.i. water | q.s. | q.s. | q.s. | q.s. | q.s. |
| pH | 4.2 | 4.2 | 4.2 | 4.2 | 4.2 |

TABLE 2

| sodium secondary alkane sulfonate (60%) | secondary alkane sulfonate, sodium salt (60% wt. actives) supplied by Hostapur SAS-60 (ex. Clariant or Nease Performance Chem.) |
| --- | --- |
| sodium lauroyl sarcosinate (30%) | lauroyl sarcosinate, sodium salt (30% wt. actives) supplied by Crodasinic LS30 NP (ex. Croda) |
| sodium cumene sulfonate (40%) | sodium cumene sulfonate, sodium salt (40% wt. actives), supplied by Eltesol SC 40 (ex. Huntsman Co.) or Naxonate 40SC (ex. Nease Performance Chemicals) |
| sodium lauryl ether sulfate 2EO (70%) | sodium lauryl ether sulfate 2EO (70% wt. actives) supplied by Texapon N70A (ex. BASF) |
| cocoamidopropyl betaine (30%) | cocoamidopropyl betaine (30% wt. actives) supplied by Mackam-35 (ex. Rhodia) |
| lactic acid (90%) | lactic acid, (90% wt. actives) supplied by lactic acid |
| PEG-4 rapeseedamide (95%) | PEG-4 rapeseedamide (95% wt. actives) supplied by Amedent-N (ex. KAO) |
| glycerine | glycerine, USP or technical grade (98-100% wt. actives) |
| NaOH (aq. soln.) (30%) | aqueous sodium hydroxide solution, (30% wt. actives) technical grade NaOH |
| sodium chloride | anhydrous sodium chloride (99-100% wt. actives), laboratory grade |
| tetrasodium glutamate diacetate (47%) | tetrasodium glutamate diacetate (47% wt. actives) supplied by Dissolvine GL-47 (ex. AkzoNobel) |

TABLE 2-continued

| preservative 1 | mixture of caprylyl glycol and ethylhexylglycerin supplied as Sensivia SC10 (ex. Schulke+ Mayr) and used "as supplied" |
| preservative2 | proprietary blend of benzyl alcohol, benzoic acid and sorbic acid supplied as Microcare SBB (ex. Thor Specialties Inc.) and used "as supplied" |
| fragrance | proprietary composition(s) of its respective supplier |
| d.i. water | deionized water |

The compositions of Tables 1A and 1B were formed, or may be formed by adding measured amounts of the identified constituent to a mixing vessel, e.g. a laboratory beaker of suitable capacity supplied with a mixing device, e.g. a motorized stilTer and mixing allowed to continue until a homogenous composition is formed. Preferably however the compositions of Table 1A and 1B are formed by adding to a beaker the water, at room temperature and under moderate stirring measured amounts of the indicated constituents, and preferably the lactic acid is the final constituent to be added, unless a minor amount of sodium hydroxide is required to adjust the final pH of the composition. Stirring is maintained until the resultant composition is homogenous, and thereafter it may be stored in a suitable container or vessel until used, or may be used immediately if so desired.

Preferred embodiments of the inventive compositions are stable upon storage at room temperature (20° C.-25° C.) for at least 90 days, preferably even longer without exhibiting an undesired degradation in physical or antimicrobial properties.

Antimicrobial Testing:

A sample of the composition El of Table IA was tested for antimicrobial efficacy against one or more of: *Staphylococcus aureus* (ATTC 6538), *Escherichia coli* (ATCC 10536)), *C. albicans* (ATCC#10231), and *K. pneumoniae* (ATCC#4352) in accordance with the protocols of British Standard EN 1276, a quantitative suspension test for the evaluation of bactericidal activity of chemical disinfectants and antiseptics used in food, industrial, domestic and institutional environments—Test Method and requirements (phase 2, step 1) Ref. No. EN 1276: 1997E the contents of which are herein incorporated by reference. The data obtained from the EN 1276 test was then used in subsequent calculations.

The $Log_{10}$ Average CFU/mL and the Average CFU/mL of the average of the plate counts for the Initial Population, Final Population, and Post-Exposure Populations versus each test product dilution were calculated according to the following equations:

$$CFU/mL = (C_i \times 10^{-D})$$

$$Log_{10} \text{ Average} = log_{10}(C_i \times 10^{-D})$$

where:

$C_i$ = Average of the plates counted

D = Dilution Factor of the plates counted

The $Log_{10}$ Reduction attributable to each test product dilution at each timed exposure was calculated according to the following equations:

$$Log_{10} \text{ Reduction} = Log_{10} \text{ Average (IP)} - Log_{10} \text{ Average (PEX)}$$

where:

IP=Average CFU/mL of the Initial Population

PEX=Average CFU/mL of the Post-Exposure Population

The results of the testing and calculations are reported on the following Table 3 where several Log 10 Reduction are reported for a particular formulation it is to be understood that two or more replicates of the identified formula were tested.

TABLE 3

| Micro (EN 1276) | E1 |
| --- | --- |
| S. aureus | >5.22, >5.22 |
| E. coli | >5.42, >5.42 |
| C. albicans | 0.73, 0.88 |
| K. pneumoniae | >5.12, >5.12 |

As is seen from the foregoing reported results, the inventive compositions exhibited excellent antimicrobial efficacy against the identified species of challenge organisms.

The composition of Table 1A also demonstrated a low degree of topical irritation, which is of particular importance with regard to consumer acceptance of

The invention claimed is:

1. An acidic feminine intimate cleansing composition effective in treating the vaginal region of the female body and the vagina, the composition having a pH in the range of from 3.5 to 5, comprising:
   as a primary antimicrobial active constituent one or more of: lactic acid and/or a substituted lactic acid and/or a salt and/or a derivative thereof;
   and a ternary anionic constituent system comprising (a) a secondary alkane sulfonate compound, (b) an N-acyl sarcosinate compound, and (c) an aromatic hydrotrope compound, wherein in the components (a), (b), and (c) of the ternary anionic constituent system are present in relative parts by weight of (a):(b):(c) in the range of : 0.5-4.5:0.025-0.25:1,
   with the proviso that salicylic acid, salicylic acid salts and salicylic acid derivatives are excluded from the compositions.

2. A composition according to claim 1, wherein in the components (a), (b) and (c) of the ternary anionic constituent system are present in relative parts by weight of (a):(b):(c) in the range of: 0.5-4:0.025-0.25:1.

3. An acidic feminine intimate cleansing composition effective in treating the vaginal region of the female body, and the vagina, the composition having a pH in the range of from 3.5 to 5, comprising:
   as a primary antimicrobial active constituent one or more of: lactic acid, and/or a substituted lactic acid and/or a salt and/or a derivative thereof;
   and a binary anionic constituent system which necessarily comprises one comprises (a) a secondary alkane sulfonate and (c) an aromatic hydroptrope compound in relative parts by weight of (a):(c) in the range of: 0.5-4.5:1
   or
   (b) an N-acyl sacrosinate compound and (c) aromatic hydroptrope compound in relative parts by weight of (b):(c) in the range of : 0.025-0.25:1
   with the proviso that salicylic acid, salicylic acid salts and salicylic acid derivatives are excluded from the compositions.

4. A feminine intimate cleansing composition according to claim 1, wherein the composition exhibits antimicrobial efficacy against one or more of *S.aureus, E.coli, C.albicans* and/or *K.pneumoniae*.

5. A feminine intimate cleansing composition according to claim 3, wherein the composition exhibits antimicrobial efficacy against one or more of *S.aureus, E.coli, C.albicans* and/or *K.pneumoniae*.

6. The composition of claim 3, wherein the (c) aromatic hydrotrope compound(s) is a cumene sulfonate compound.

7. A composition according to claim 1 wherein:

the (a) secondary alkane sulfonate compound is present in excess of that of the (c) aromatic hydrotrope compound, and at the same time the (b) N-acyl sarconsinate compound, are present in an amount at least about 74% less than the (c) aromatic hydrotrope compound.

8. The composition according to claim 7, which exhibits antimicrobial efficacy against one or more of *S.aureus, E.coli, C.albicans* and/or *K.pneumoniae*.

9. The composition of claim 1, wherein the (c) aromatic hydrotrope compound is a cumene sulfonate compound.

10. The composition of claim 1, wherein the composition is not disruptive of the naturally occurring bacterial flora within the vagina.

11. The composition of claim 10, wherein the composition is not disruptive of *Lactobacilli* already present within the vagina.

12. The composition in claim 1, wherein the composition excludes cationic compounds which independently provide an antimicrobial benefit.

13. The composition of claim 1, wherein the composition exhibits efficacy against microorganisms of the genus *Candida*.

* * * * *